US010807954B2

(12) United States Patent
Minke et al.

(10) Patent No.: US 10,807,954 B2
(45) Date of Patent: Oct. 20, 2020

(54) METHOD FOR PREPARING TRIACETONE AMINE

(71) Applicant: Evonik Operations GmbH, Essen (DE)

(72) Inventors: Katharina Minke, Essen (DE); Julia Rieb, Muenster (DE); Manfred Neumann, Marl (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/702,667

(22) Filed: Dec. 4, 2019

(65) Prior Publication Data
US 2020/0181088 A1  Jun. 11, 2020

(30) Foreign Application Priority Data

Dec. 7, 2018 (EP) ..................................... 18210919

(51) Int. Cl.
C07D 211/74 (2006.01)

(52) U.S. Cl.
CPC ................................. *C07D 211/74* (2013.01)

(58) Field of Classification Search
CPC .................................................. C07D 211/74
USPC ........................................................ 546/242
See application file for complete search history.

(56) References Cited

U.S. PATENT DOCUMENTS

| | | | |
|---|---|---|---|
| 3,943,139 A | 3/1976 | Orban et al. | |
| 3,953,459 A | 4/1976 | Orban et al. | |
| 3,960,875 A | 6/1976 | Orban et al. | |
| 4,275,211 A * | 6/1981 | Orban ................... | C07D 211/74 546/242 |
| 4,831,146 A | 5/1989 | Taylor et al. | |
| 5,773,622 A | 6/1998 | Jegelka et al. | |
| 9,617,245 B2 | 4/2017 | Niemeyer et al. | |
| 9,868,702 B2 | 1/2018 | Rüfer et al. | |
| 10,227,300 B2 | 3/2019 | Willy et al. | |
| 10,252,978 B2 | 4/2019 | Minke et al. | |
| 10,358,420 B2 | 7/2019 | Minke et al. | |
| 2016/0214937 A1 | 7/2016 | Willy et al. | |
| 2016/0214962 A1 | 7/2016 | Niemeyer et al. | |
| 2017/0355674 A1 | 12/2017 | Rüfer et al. | |
| 2018/0009734 A1 | 1/2018 | Minke et al. | |
| 2018/0009752 A1 | 1/2018 | Minke et al. | |

FOREIGN PATENT DOCUMENTS

| | | |
|---|---|---|
| CA | 666225 | 7/1963 |
| CA | 668290 | 8/1963 |
| CA | 677298 | 12/1963 |
| CA | 722240 | 11/1965 |
| CN | 1336365 | 2/2002 |
| CN | 102516158 | 6/2012 |
| CN | 103224465 | 4/2015 |
| CN | 107033066 | 8/2017 |
| CN | 108383704 | 8/2018 |
| CN | 108383776 | 8/2018 |
| CN | 108409637 | 8/2018 |
| CN | 108484482 | 9/2018 |
| CN | 108484483 | 9/2018 |
| CN | 109746004 | 5/2019 |
| DE | 2 352 127 | 4/1974 |
| DE | 24 29 935 | 1/1975 |
| DE | 24 29 936 | 1/1975 |
| DE | 31 35 489 | 3/1983 |
| DE | 24 29 937 | 1/1988 |
| EP | 0 004 104 | 9/1979 |
| EP | 0 033 529 | 8/1981 |
| EP | 0 074 607 | 3/1983 |
| EP | 2 706 056 | 3/2014 |
| GB | 1 461 703 | 1/1977 |
| JP | 54-88275 | 7/1979 |
| JP | 54-112873 | 9/1979 |
| JP | 4-154762 | 5/1992 |
| JP | 2001-31651 | 2/2001 |
| JP | 2003-206277 | 7/2003 |
| MY | 160047 | 2/2017 |

OTHER PUBLICATIONS

Extended European Search Report dated Feb. 22, 2019 in European Application No. 18210919.9, with English translation, 10 pages.
Song et al., Chemical Industry and Engineering, vol. 16, No. 4, Aug. 1999, 239-241, with English Translation, 7 pages.
Du et al., Asian Journal of Chemistry; vol. 27, No. 2 (2015), 541-543.
Huang et al., Science & Technology in Chemical Industry, 1999, 7(4):49-51, with English Translation, 8 pages.
Li et al., Shandong Chemical Industry, vol. 38, No. 8, 2009, 10-11, with English Translation, 6 pages.
Quan et al., Journal of East China University of Science and Technology (Natural Science Edition), vol. 38, No. 6, Dec. 2012, 698-701, 717, with English Translation, 13 pages.
Rozantsev et al., Chemical-pharmaceutical journal, 1969, 5, 47-51, with English Translation, pp. 10.
Son et al., Chemical Industries, Issue 89, 2003, 559-564.
Sosnovsky et al., Z. Naturforsch. 32 b, 328-337 [1977]; received Nov. 29, 1976.
Sosnovsky et al., Z. Naturforsch. 32 b, 338-346 [1977]; received Nov. 29, 1976.

(Continued)

*Primary Examiner* — Nizal S Chandrakumar
(74) *Attorney, Agent, or Firm* — Grüneberg and Myers PLLC

(57) ABSTRACT

An improved method is used for preparing triacetone amine while recycling the by-products. This involves treating the crude product from triacetone amine preparation, which leads to an increase in the content of compounds which react readily with ammonia. This method enables efficient recycling of the by-products formed in the synthesis of triacetone amine.

12 Claims, No Drawings

(56) References Cited

OTHER PUBLICATIONS

Wei et al., Natural Gas Chemical Industry, Fine Chemicals Industry, vol. 16, No. 4, 1991, 46-49, with English Translation, pp. 11.
Xia et al., Plastic Additives, Production and Equipment, vol. 5, No. 59, 2006, 46-48, with English Translation, 8 pages.
U.S. Pat. No. 10,227,300, Mar. 12, 2019, 2016/0214937, Willy et al.
U.S. Pat. No. 9,617,245, Apr. 11, 2017, 2016/0214962, Niemeyer et al.
U.S. Pat. No. 9,868,702, Jan. 16, 2018, 2017/0335674, Rüfer et al.
U.S. Pat. No. 10,252,978, Apr. 9, 2019, 2018/0009734, Minke et al.
U.S. Pat. No. 10,358,420, Jul. 23, 2019, 2018/0009752, Minke et al.
Wu et al., Synthetic Communications; 1996, 26(19):3565-3569.

* cited by examiner

METHOD FOR PREPARING TRIACETONE AMINE

CROSS-REFERENCE TO RELATED APPLICATIONS

The present application claims the benefit of the European Application EP18210919.9, filed on Dec. 7, 2018, which is incorporated by reference in its entirety.

BACKGROUND OF THE INVENTION

Field of the Invention

The present invention relates to an improved method for preparing triacetone amine. This involves treating the crude product from triacetone amine preparation, which leads to an increase in the content of compounds which react readily with ammonia. This method enables efficient recycling of the by-products formed in the synthesis of triacetone amine.

Discussion of the Background

Triacetone amine (2,2,6,6-tetramethyl-4-piperidinone; CAS number: 826-36-8; hereinafter "TAA") is an important chemical intermediate which is used for the synthesis of numerous derivative products, for example light stabilizers (hindered amine light stabilizers; [HALS]), oxidizing agents and polymerization moderators (e.g. nitroxyl radicals).

The preparation of triacetone amine from acetone and ammonia has been documented in the form of different methods. This includes the preparation methods of direct (single-step) synthesis of TAA from the reactants, for example described in DE 24 29 937 A1, U.S. Pat. No. 4,536,581 A, JPS54-88275 A or in Zeitschrift für Naturforschung 1976, 328-337 and 338-345, and also indirect (two-step) synthesis via acetonin (2,2,4,4,6-pentamethyl-1,2,5,6-tetrahydropyrimidine), for example described in DE 24 29 935 A1 or DE 24 29 936 A1, or via phorone (2,6-dimethyl-2,5-heptadien-4-one), e.g. described in DE 2 352 127 A1. In the two-step TAA synthesis via acetonin, acetonin is firstly formed from acetone and ammonia, and then reacts further in a subsequent step, with cleavage of one equivalent of ammonia, to give TAA. In the case of the synthesis method via acetonin, however, while both species (TAA and acetonin) are always formed simultaneously, acetonin formation is nonetheless greatly kinetically favoured over TAA formation. In the "single-step" TAA synthesis, acetonin is merely not isolated.

The preparation of TAA is in principle equally possible whether catalysed homogeneously (mainly by ammonium salts) or heterogeneously (e.g. on acidic ion exchangers).

Most documents from the related art relate to homogeneously-catalysed reactions. The most commonly mentioned in this case are calcium chloride (e.g. in Chemical Industries 2003, 89, 559-564; Zeitschrift für Naturforschung 1976, 328-337 and 338-345), ammonium chloride (e.g. in JP 2003-206277 A; JP 2001-31651 A; JPH4-154762 A) and hydrazine derivatives (e.g. in JPS54-88275 A, JPS54-112873 A). However, problems arise when using these catalysts. Thus, for example, the use of calcium chloride has the disadvantage of a very slow reaction taking place. In the case of ammonium chloride, the reaction rate is higher but the chloride used exhibits very high corrosiveness in relation to steel. Hydrazine derivatives, on the other hand, exhibit very high toxicity.

In contrast, reactions on heterogeneous catalysts have also been described, for example in DE 28 07 172 A1 and CN 103224465 A.

TAA is generally prepared in a matrix in which the acetone is present in a large excess and serves as both reaction partner and solvent. Therefore, at the end of the reaction there results a crude product which, aside from TAA, contains a large proportion of acetone, unreacted ammonia, water formed by the condensation, and, in homogeneously-catalytic methods, the catalyst. In addition, further secondary components are present, e.g. acyclic condensation products (e.g. diacetone alcohol, diacetone amine, mesityl oxide, phorone, etc.), cyclic condensation products [e.g. acetonin, 2,2,4,6-tetramethyl-2,3-dihydropyridine (hereinafter "TMDH pyridine")] or higher molecular weight condensation products ("high boilers").

Some acyclic addition and condensation products (e.g. diacetone alcohol [4-hydroxy-4-methylpentan-2-one], diacetone amine [4-amino-4-methylpentan-2-one], mesityl oxide [4-methylpent-3-en-2-one], phorone, etc.) may, for their part, be reacted instead of acetone as reactants with ammonia to give TAA, which is utilized for example in methods with a process-internal recycling stream (DE 28 07 172 A1).

In addition, the related art describes TAA syntheses proceeding from acetone or also these acetone condensation products.

CN 108383704 A describes the batchwise use of the by-products formed in the synthesis of TAA for the preparation of acetone, which can then in turn be used as starting material. In this case, water is added to the by-product mixture in the presence of a catalyst, and the by-products are cleaved.

CN 108484483 A describes a method for purifying TAA which combines distillation and crystallization.

CN 108383776 A describes the removal and re-use of the by-products formed in the synthesis of TAA in subsequent TAA synthesis steps.

However, the use of these by-products as starting materials does entail some problems. Firstly, they have lower reactivity and in part react very much more slowly than acetone. Only mesityl oxide has comparable reactivity to acetone. The use of these compounds as starting materials for the synthesis of further TAA is therefore disadvantageous precisely in large-scale industrial methods.

Secondly, a further disadvantage of the conventional methods for TAA synthesis is that the described by-products are expensive to remove from excess acetone and the desired product TAA. The boiling points of the typical by-products diacetone alcohol (CAS number 123-42-2; boiling point at standard pressure: 166° C.), acetonin (CAS number 556-72-9; boiling point ~170° C.), diacetone amine (CAS number 625-04-7, boiling point ~180° C.), phorone (CAS number 504-20-1; boiling point at standard pressure: 197° C.) are 30 between the boiling points of acetone (CAS number 67-64-1; boiling point at standard pressure: 56° C.) or mesityl oxide (CAS number 141-79-7; boiling point at standard pressure: 130° C.) and TAA (boiling point at standard pressure: 205° C.), and in the case of isophorone (CAS number 78-59-1; boiling point at standard pressure: 215° C.) even greater than these.

As a result, the purification of the TAA from the reaction mixture obtained is complicated. In distillative purification, many distillation stages are necessary in order to remove the desired product TAA in as pure a form as possible and as completely as possible from the by-products. This in turn requires expensive distillation apparatus, for example a column with a high number of theoretical plates.

There was therefore the need for an efficient method for synthesizing TAA which does not have the abovementioned problems and in particular provides a TAA product which is as pure as possible while simultaneously enabling the efficient re-utilization of the by-products obtained in the TAA synthesis.

SUMMARY OF THE INVENTION

The abovementioned object is achieved by means of the present invention. In particular, it was determined, surprisingly, that a particularly efficient method for preparing TAA is enabled by the by-products obtained in the preparation of TAA from acetone and ammonia being reacted with water and the crude product thereby being enriched in species which are particularly reactive in the reaction with ammonia to give further TAA. Moreover, it was demonstrated, surprisingly, that the distillative removal of the acetone and other enriched species such as mesityl oxide from the crude product treated in this way can be carried out much more efficiently, and thus these can be recycled better.

This was all the more surprising since the crude product from the reaction of ammonia with acetone to give TAA comprises water. In order to realize the advantageous effect of the invention, however, the addition of additional water is necessary.

Accordingly, the inventive method is a method for preparing triacetone amine, comprising the following steps:

(a) reaction of acetone and ammonia in the presence of a catalyst K1 to give a crude product RP1 comprising triacetone amine, acetone and mesityl oxide and at least one by-product selected from the group consisting of diacetone alcohol, diacetone amine, acetonin, phorone, isophorone, (b) at least partial distillative removal of acetone and/or mesityl oxide from RP1, (c) addition of ammonia and optionally further acetone to the acetone and/or mesityl oxide removed from RP1 in step (b), and at least partial reaction of the added ammonia with acetone and/or mesityl oxide in the presence of a catalyst K2 to give TAA, as a result of which a crude product RP2 comprising triacetone amine is obtained, characterized in that (d) before and/or during the distillative removal of acetone and/or mesityl oxide from RP1 occurring in step (b), water is added to RP1 in step (b) and at least one of the by-products in RP1, selected from the group consisting of diacetone alcohol, diacetone amine, acetonin, phorone, isophorone, is at least partially reacted with water, such that at least one of the by-products in RP1 is at least partially cleaved into mesityl oxide and/or acetone.

The present invention includes the following embodiments:

1. Method for preparing triacetone amine, comprising the following steps:

(a) reaction of acetone and ammonia in the presence of a catalyst K1 to give a crude product RP1 comprising triacetone amine, acetone, mesityl oxide and at least one by-product selected from the group consisting of diacetone alcohol, diacetone amine, acetonin, phorone, isophorone, (b) at least partial distillative removal of acetone and/or mesityl oxide from RP1, (c) addition of ammonia and optionally further acetone to the acetone and/or mesityl oxide removed from RP1 in step (b), and at least partial reaction of the added ammonia with acetone and/or mesityl oxide in the presence of a catalyst K2 to give TAA, as a result of which a crude product RP2 comprising triacetone amine is obtained, characterized in that (d) before and/or during the distillative removal of acetone and/or mesityl oxide from RP1 occurring in step (b), water is added to RP1 and at least one of the by-products in RP1, selected from the group consisting of diacetone alcohol, diacetone amine, acetonin, phorone, isophorone, is at least partially reacted with water, such that at least one of the by-products in RP1 is at least partially cleaved into mesityl oxide and/or acetone.

2. Method according to embodiment 1, wherein, in step (d), during the distillative removal of acetone and/or mesityl oxide from RP1 occurring in step (b), water is added to RP1 and at least one of the by-products in RP1, selected from the group consisting of diacetone alcohol, diacetone amine, acetonin, phorone, isophorone, is at least partially reacted with water, such that at least one of the by-products in RP1 is at least partially cleaved into mesityl oxide and/or acetone.

3. Method according to either of embodiments 1 and 2, wherein the at least partial distillative removal of acetone and/or mesityl oxide from RP1 occurring in step (b) takes place in a distillation column.

4. Method according to embodiment 3, wherein the temperature range used in the distillation in step (b) is below the boiling point of triacetone amine.

5. Method according to one of embodiments 1 to 4, wherein step a) is carried out at a temperature of 20° C. to 180° C.

6. Method according to one of embodiments 1 to 5, wherein the molar ratio of acetone used in step (a) to ammonia used in step (a) is 3:1 to 20:1.

7. Method according to one of embodiments 1 to 6, wherein K11 is a heterogeneous catalyst.

8. Method according to one of embodiments 1 to 7, wherein the amount of water added in step (d) is ≥0.1 wt %, based on the sum of the weights of phorone, diacetone alcohol, diacetone amine, acetonin and isophorone contained in RP1.

9. Method according to one of embodiments 1 to 8, wherein the reaction in step (c) is carried out at a temperature of 20° C. to 180° C.

10. Method according to one of embodiments 1 to 9, wherein K2 is a heterogeneous catalyst.

11. Method according to one of embodiments 1 to 10, wherein, in step (c), ammonia is added in an overall amount such that, for each mole of acetone used in step (c), 0.05 to 0.33 mol of ammonia is added, and in addition to this ammonia added for acetone, for each mole of mesityl oxide used in step (c), 0.1 to 0.66 mol of ammonia is added.

DETAILED DESCRIPTION OF THE INVENTION

1. Step (a)

In step (a) of the inventive method, acetone and ammonia are reacted in the presence of a catalyst K1.

This gives a crude product RP1 comprising triacetone amine. This also comprises, in addition to the desired product TAA, unreacted acetone and also mesityl oxide as by-product. Mesityl oxide is the simplest condensation product which is always formed, at least in small amounts, in the reaction of ammonia and acetone to give TAA by aldol condensation of two molecules of acetone. Higher molecular weight condensation products of acetone with itself or ammonia are also formed in the reaction in step (a) and are therefore included in the crude product RP1. These are predominantly by-products selected from the group consisting of diacetone alcohol, diacetone amine, acetonin, phorone, isophorone, preferably selected from the group consisting of diacetone alcohol, diacetone amine, acetonin and isophorone.

The reaction in step (a), like the entire inventive method, can be carried out continuously or in batchwise operation.

In the case of batchwise operation, all reactants are preferably added together, then the reaction mixture is heated. In this case, all customary types of reactor are suitable as reactor, e.g. stirred reactors, loop reactors, or reactors with internal heat exchangers.

In continuous operation, all chemicals are preferably metered in simultaneously at the reaction temperature. In continuous reaction, any reactor known to those skilled in the art can be used, e.g. a continuous flow tube, a continuous stirred tank, a stirred tank cascade, and also possible combinations of these individual elements. In this case preference is given to using a combination of one or more reactors with internal or external circuit, followed by a downstream reactor with flow tube characteristics.

The reaction time in step (a) in batchwise operation is in the range of 1 to 15 hours, preferably in the range of 3 to 9 hours, particularly preferably in the range of 5 to 7 hours.

The reaction times for the continuous method operation are given by the total residence time of the reactants in the reactor and are in the range stated for batchwise operation.

The "volume space velocity," for ammonia in continuous operation is, in step (a), especially 0.01 to 124.20 $h^{-1}$, preferably 0.03 to 5.25 $h^{-1}$, most preferably 0.06 $h^{-1}$ (this corresponds to the volume of ammonia flowing through this reactor per hour and per volume of the reactor, abbreviated to "LHSV").

The "volume space velocity" for acetone in continuous operation is, in step (a), especially 0.15 to 1.33 $h^{-1}$, preferably 0.66 to 1.17 $h^{-1}$ (this corresponds to the volume of acetone flowing through this reactor per hour and per volume of the reactor).

The reaction in step (a) can take place in the presence of further solvents or just in acetone, i.e. without the addition of further solvents. In cases in which a solvent is used in step (a), all solvents which do not impede the reaction can be used. In particular, the possible solvents are aliphatic solvents, preferably pentane, hexane, heptane, octane, decane, cyclohexane, tetramethylsilane; aromatic solvents, preferably benzene, toluene, xylene; ether compounds, preferably diethyl ether, dipropyl ether, dibutyl ether, methyl-tert-butyl ether; halogenated solvents, preferably dichloromethane, chloroform, tetrachloromethane; alcohols, preferably methanol, ethanol, propanol, isopropanol, butanol, tert-butanol; esters, preferably methyl acetate, ethyl acetate, propyl acetate, butyl acetate. Particularly preferably, the reaction in step (a) takes place in acetone without the addition of further solvents.

The reaction in step (a) is preferably carried out at elevated temperature, especially at temperatures in the range of 20° C. to 180° C., preferably in the range of 40° C. to 100° C., more preferably in the range of 55° C. to 90° C., even more preferably in the range of 60° C. to 90° C., most preferably at 75° C.

The reaction in step (a) is especially either carried out at the autogenous pressure of the components or at elevated pressure. Thus, the reaction in step (a) is preferably carried out at a pressure in the range of 1 to 16 bar, more preferably at a pressure in the range of 1 to 15 bar, even more preferably at a pressure in the range of 7 to 14 bar, even more preferably still at 12 bar.

Ammonia is preferably metered in in step (a) of the inventive method as pure substance, i.e. as gas, and is especially present during the reaction dissolved in acetone or dissolved in the reaction mixture.

Acetone is preferably metered in in step (a) as pure substance. Alternatively, acetone can be used which was removed in step (b) of a previous round of the inventive method and is thereby recycled. It goes without saying, that condensation products of the acetone with itself or ammonia may then be present in the reaction solution in step (a) alongside acetone and ammonia. These condensation products may originate from previous steps of reaction of ammonia and acetone to give TAA.

Step (a) of the inventive method is carried out in the presence of a catalyst K1. All catalysts mentioned in the related art for this type of reaction are suitable as catalyst K1. In this case, the catalyst K1 can be homogeneous or heterogeneous, but is preferably heterogeneous.

All homogeneous catalysts described in the related art for this type of reaction are suitable as homogeneous catalyst K1, e.g. Brønsted acids, salts of these acids or Lewis acids, as described in EP 2 706 056 A1.

The term "Brønsted acids" in the context of the invention includes especially hydrochloric acid, sulfuric acid, nitric acid, organic acids (RCOOH) or sulfonic acids (RSO$_3$H), with R being selected from the group consisting of saturated, unsaturated, branched, unbranched, ring-closed, open-chain aliphatic, aromatic, substituted or unsubstituted hydrocarbon radicals. Substituted hydrocarbon radicals in the context of the invention are hydrocarbon radicals substituted with heteroatoms, especially hydrocarbon radicals substituted with one or more —OH, —NH, —CN, alkoxy and/or halogen radicals, preferably substituted with one or more halogen radicals, particularly preferably substituted with one or more radicals selected from F, Cl, Br and I, most particularly preferably substituted with one or more radicals selected from F and Cl.

"Salts of a Brønsted acid" in the context of the invention are especially ammonium salts (i.e. salts with ammonia, amines, hydrazines, hydroxylamines) or phosphonium salts (i.e. salts with phosphanes). Lewis acids in the context of the invention are especially compounds from the 4th or 13th group of the periodic table, preferably halides (AlCl$_3$, BF$_3$, TiCl$_4$), alkoxides [Al(OR*)$_3$, B(OR*)$_3$, Ti(OR*)$_4$] or alkyl compounds (e.g. AlR*$_3$), with R* being selected from the group consisting of saturated, unsaturated, branched, unbranched, ring-closed, open-chain aliphatic, aromatic, substituted or unsubstituted hydrocarbon radicals.

Lewis acids in the context of the invention are also salts of Lewis-acidic alkali metals or alkaline earth metals (e.g. CaCl$_2$, MgCl$_2$, LiCl).

Preference is given, in cases in which K1 is a homogeneous catalyst, to said catalyst being selected from the group of ammonium salts, especially from the group comprising salts of ammonia and strong Brønsted acids [e.g. hydrochloric acid, sulfuric acid, nitric acid, organic acids (RCOOH) or sulfonic acids (RSO$_3$H), with R** being selected from the group consisting of saturated, unsaturated, branched, unbranched, ring-closed, open-chain aliphatic, aromatic, substituted or unsubstituted hydrocarbon radicals].

Preference is given, in cases in which K1 is a homogeneous catalyst, to said catalyst being ammonium nitrate. Ammonium nitrate has the advantage of being cheap, non-toxic, halide-free and hence less corrosive.

As catalyst K1, however, preference is given to using a heterogeneous catalyst, especially a solid acidic catalyst as for example described in DE 28 07 172 A1, CN 103224465

A or DE 10 2010 062 804 A1. These are catalysts which are practically insoluble in the reaction medium. For this purpose, preference is given to using a catalyst which is inorganic or organic and has active acid groups, preferably sulfonic ester groups or phosphoric ester groups.

K1 is accordingly especially selected from the group consisting of aluminium hydrosilicates of bentonite and/or montmorillonite type, inorganic ion exchangers based on aluminium silicate of zeolite type, mordenite type, erionite type or else diatomaceous earth treated with phosphoric acid at 700 to 1100° C., as described in CA 772 201.

Heterogeneous catalysts that are particularly preferred for K1 are ion exchange resins, especially cation exchange resins. These are preferably acidic.

Ion exchange resins for K1 include especially those which are inorganic-based (for example silicon dioxide) or organic-based (for example polystyrene or polystyrene copolymers, such as styrene-divinylbenzene copolymers), preferably organic-based, which have protic acid groups, especially alkylsulfonic ester groups, sulfonic ester groups ($—SO_3^-$), phosphoric ester groups, especially sulfonic ester groups.

A particularly preferred heterogeneous catalyst for K1 is selected from the following group:

A catalyst having a polymer resin, especially polystyrene or styrene-divinylbenzene copolymer, preferably polystyrene, and protic acids, especially $—SO_3^-$ groups, as functional groups (commercially available as Amberlyst® 15, Amberlite® 200, Lewatit® SP 120 or Lewatit®, K2621); use may also be made alongside this of polystyrene sulfonate with the CAS number: 28210-41-5;

A catalyst having protic acids, especially sulfonic acid in polymeric form and which can be perfluorinated (described in DE 10 2010 062 804 A1, U.S. Pat. No. 4,831,146). This may for example be a sulfonated tetrafluoroethylene (CAS number: 31175-20-9) or a solid supported perfluorinated sulfonic acid in polymeric form with silicon dioxide as carrier material. Such catalysts are, inter alia, available under the trade names Nafion®, Aciplex® F, Femion®, Neosepta®, Fumion® F. A preferred catalyst is Nafion® SAC-13. Nafion® SAC-13 is porous silicon dioxide particles onto which Nafion® has been adsorbed in a charge of approximately 13 wt %;

Poly(2-acrylamido-2-methyl-1-propanesulfonic acid), sold as PolyAMPS® by Lubrizol.

Use is most preferably made, as K1, of a heterogeneous catalyst having a polymer resin, especially polystyrene or styrene-divinylbenzene copolymer, preferably polystyrene, and protic acids, especially $—SO_3^-$ groups, as functional groups (commercially available as Amberlyst®) 15, Amberlite® 200, Lewatit® SP 120 or Lewatit® K2621).

The use ratios of the reactants in step (a) of the inventive method can be selected in broad ranges; acetone is especially used in excess relative to ammonia. Preferably, the molar ratio of acetone used in step (a) to ammonia used in step (a) is 3:1 to 20:1, with a ratio of 6:1 to 10:1 being preferred and a ratio of 7:1 being particularly preferred.

The amount of catalyst K1 used is not particularly restricted and can be determined by those skilled in the art. Typically, if the catalyst is a homogeneous catalyst from the group of the Brønsted acids, salts of these acids or Lewis acids, preferably an ammonium salt, even more preferably is ammonium nitrate, the latter can be used in a molar ratio of ammonia to catalyst, preferably ammonium nitrate, in the range of 1:0.8 to 1:0.02. Most particularly preferably, the molar ratio of acetone:ammonia:ammonium nitrate is in the range of 7 to 8:0.9 to 1.1:0.085 to 0.098.

In the preferred embodiment, in which a solid, acidic ion exchanger is used for K1, the latter can be used as a fixed bed, for example at an amount of 10 to 20 vol % based on the total amount of the acetone used in step (a) and—if such was used—the mesityl oxide.

At the end of step (a) of the inventive method, a crude product RP1 is then obtained which, alongside the desired product triacetone amine, also contains the originally used reactant acetone, and also mesityl oxide as by-product and at least one by-product selected from the group consisting of diacetone alcohol, diacetone amine, acetonin, phorone, isophorone, preferably selected from the group consisting of diacetone alcohol, diacetone amine, acetonin, phorone and isophorone.

The proportion of the TAA, acetone, mesityl oxide, water and the stated by-products in RP1 is not further restricted and results from the stoichiometry and the specific reaction conditions. The proportion of the respective compound can be determined by GC. For example, after the reaction there is a mixture containing the content of acetone of 55 to 60 wt %, of mesityl oxide of 10 wt %, of TMDH pyridine of 5 to 6 wt %, of the sum of diacetone amine, acetone alcohol and phorone of 4 to 6 wt %/o, of TAA of 14 to 16 wt %, and of components boiling higher than TAA (for example isophorone) of 3 to 4 wt %, and the proportion of water is 7 wt %.

2. Step (b)

In step (b) of the inventive method, acetone and/or mesityl oxide are at least partially removed from RP1. This is carried out distillatively, preferably in a distillation column.

During or before, preferably before, step (b), the catalyst K1 is also optionally removed. This may occur by addition of a base. For example, NaOH is added if K1 is an ammonium salt, and the sodium nitrate which then precipitates out is subsequently removed.

When using a heterogeneous catalyst, a separate purification step is superfluous or is at least significantly easier, since for example when using a fixed bed catalyst, this catalyst remains in the reactor or in other cases can remain in the reaction tank and/or can be removed by filtration. For this reason also, the use of a heterogeneous catalyst for K1 is to be preferred.

3. Step (d)

The invention is now based on the fact that before and/or during step (b), i.e. the distillative removal of acetone and/or mesityl oxide from RP1, water is added to RP1 and at least one of the by-products in RP1, selected from the group consisting of phorone, diacetone alcohol, diacetone amine, acetonin, isophorone, preferably selected from the group consisting of diacetone alcohol, diacetone amine, acetonin, isophorone, is at least partially reacted with water, such that at least one of the by-products in RP1 is at least partially cleaved into mesityl oxide and/or acetone. This step is referred to hereinafter as "step (d)".

Step (d) of the inventive method ensures that at least one of the less reactive by-products in RP1, i.e. at least one selected from the group consisting of diacetone alcohol, diacetone amine, acetonin, phorone, isophorone, preferably at least one selected from the group consisting of diacetone alcohol, diacetone amine, acetonin, isophorone, is reacted to give acetone and/or mesityl oxide. This leads to these mid-boiling (in the sense of "boiling between mesityl oxide and TAA") or higher-boiling (in the sense of "boiling higher than TAA") by-products, for example isophorone, decomposing to low-boiling mesityl oxide and acetone, which appreciably simplifies especially the distillative purification of the TAA from the crude product RP1.

In addition thereto, the more reactive species acetone, and the most reactive equivalent thereof, mesityl oxide, can advantageously be reacted again with ammonia to give further TAA in the subsequent steps in a significantly better way than when instead the mid-boiling and higher-boiling by-products have to be reacted with ammonia in a subsequent step to give further TAA.

According to step (d), water is added to RP1 before and/or during the distillative removal of acetone and/or mesityl oxide from RP1 which takes place in step (b). It goes without saying that the addition of water "before the removal of acetone and/or mesityl oxide from RP1" means that this point in time is between steps (a) and (b), since it is only after step (a) that the crude product RP1 is obtained.

The addition of water in step (d) is in this case essential for carrying out the invention, since as a result the equilibrium is shifted from the side of the by-products to the side of the cleavage products of the same, i.e. predominantly mesityl oxide alongside acetone. In order to ensure sufficient shifting of the equilibrium, the water resulting from the reaction in step (a) and which may still be present at least in part in RP1 is insufficient. Rather, it is necessary to add at least a specific amount of additional water to RP1 in step (d) in order to shift the equilibrium in the following reaction to the side of the desired product acetone and/or mesityl oxide.

In particular, in step (d) of the inventive method, water is added in an amount of ≥0.1 wt/o, preferably ≥0.5 wt %, more preferably ≥1 wt %, even more preferably ≥5 wt %, more preferably still in the range of 5 to 40 wt %, even more preferably still in the range of 10 to 20 wt %, in each case based on the sum of the weights of phorone, diacetone alcohol, diacetone amine, acetonin and isophorone contained in RP1. This proportion can be determined by those skilled in the art using gas chromatography. The total weight of RP1 can be determined in the continuous method by determining the flow rate (mass flow meter) and in the batchwise method by weighing.

Alternatively, in step (d) of the inventive method, water can be added in an amount of ≥1 wt %, preferably ≥3 wt %, more preferably ≥4 wt %, even more preferably ≥5 wt %, more preferably still in the range of 5 to 40 wt %, even more preferably still in the range of 10 to 20 wt %, in each case based on the total weight of the amount of acetone used in step (a) of the inventive method.

The reaction of the water added in step (d) with at least one of the by-products in RP1 selected from the group consisting of phorone, diacetone alcohol, diacetone amine, acetonin, isophorone, preferably selected from the group consisting of diacetone alcohol, diacetone amine, acetonin, isophorone, to give acetone and/or mesityl oxide, can then be carried out under the conditions familiar to those skilled in the art. This is a hydrolysis of the by-products to give mesityl oxide and/or acetone. The temperature range used for this purpose is especially <205° C., preferably <204° C., is more preferably in the range of 30° C. to 200° C., is even more preferably in the range of 70° C. to 185° C.

Preferably, according to step (d) of the inventive method, the water is added to RP1 while in step (b) acetone and/or mesityl oxide are at least partially removed from RP1.

This embodiment is even more preferable if the at least partial distillative removal of acetone and/or mesityl oxide from RP1 in step (b) takes place in a distillation column.

Even more preferably still, the reaction of the water added in step (d) with at least one of the by-products in RP1 selected from the group consisting of phorone, diacetone alcohol, diacetone amine, acetonin, isophorone, preferably selected from the group consisting of diacetone alcohol, diacetone amine, acetonin, isophorone, to give acetone and/or mesityl oxide, then takes place in the gas phase.

In this case, the water is especially supplied to the distillation column during the distillative removal, either by a supply of water into the distillation column or by addition of steam to the distillation column. The reaction of at least one of the by-products diacetone alcohol, diacetone amine, acetonin, phorone, isophorone, preferably the by-products selected from the group consisting of diacetone alcohol, diacetone amine, acetonin, isophorone, with water to give acetone and/or mesityl oxide then takes place in the distillation column.

This embodiment has proved to be particularly advantageous since this embodiment ensures particularly well that the secondary components are decomposed in a targeted manner and the undesired reverse reaction of the TAA is suppressed. This is particularly well ensured, and it is therefore preferred, if the temperature range used in the distillation in step (b) is below the boiling point of TAA, with the pressure especially being standard pressure, preferably <205° C. at standard pressure, more preferably <204° C. at standard pressure, even more preferably in the range of 30° C. to 200° C. at standard pressure, even more preferably still in the range of 70° C. to 185° C. at standard pressure.

4. Step (c)

In step (c) of the inventive method, then, ammonia and optionally acetone are added to the acetone and/or mesityl oxide removed in step (b) from RP1, and acetone and/or mesityl oxide are at least partially reacted with the added ammonia in the presence of a catalyst K2 to give TAA.

This again gives a crude product RP2 comprising triacetone amine. This also comprises in particular, alongside the desired product TAA, unreacted acetone and also mesityl oxide as by-product and also the higher molecular weight condensation products of acetone with itself or ammonia. These are predominantly by-products selected from the group consisting of diacetone alcohol, diacetone amine, acetonin, phorone, isophorone, preferably selected from the group consisting of diacetone alcohol, diacetone amine, acetonin and isophorone.

In step (c) of the inventive method, in this case, in particular, ammonia is added in an amount such that, for each mole of acetone used in step (c), 0.05 to 0.33 mol, preferably 0.10 to 0.166 mol, more preferably 0.143 mol of ammonia is added.

In addition to this ammonia added for acetone, in particular, for each mole of mesityl oxide used in step (c), 0.1 to 0.66 mol, preferably 0.25 to 0.33 mol, more preferably 0.286 mol of ammonia is added.

The reaction in step (c) can take place in the presence of further solvents or just in acetone, i.e. without the addition of further solvents. In cases in which a solvent is used in step (c), all solvents which do not impede the reaction can be used. In particular, the possible solvents are aliphatic solvents, preferably pentane, hexane, heptane, octane, decane, cyclohexane, tetramethylsilane; aromatic solvents, preferably benzene, toluene, xylene; ether compounds, preferably diethyl ether, dipropyl ether, dibutyl ether, methyl-tert-butyl ether; halogenated solvents, preferably dichloromethane, chloroform, tetrachloromethane; alcohols, preferably methanol, ethanol, propanol, isopropanol, butanol, tert-butanol; esters, preferably methyl acetate, ethyl acetate, propyl acetate, butyl acetate. Particularly preferably, the reaction in step (c) takes place in acetone without the addition of further solvents.

In continuous operation, all chemicals are preferably metered in simultaneously at the reaction temperature. In continuous reaction, any reactor known to those skilled in the art can be used, e.g. a continuous flow tube, a continuous stirred tank, a stirred tank cascade, and also possible combinations of these individual elements. In this case preference is given to using a combination of one or more reactors with internal or external circuit, followed by a downstream reactor with flow tube characteristics.

The reaction time in step (c) in batchwise operation is in the range of 1 to 15 hours, preferably in the range of 3 to 9 hours, particularly preferably in the range of 5 to 7 hours. The reaction times for the continuous method operation are given by the total residence time of the reactants in the reactor and are in the range stated for batchwise operation.

The "volume space velocity" for ammonia in continuous operation is, in step (c), especially 0.01 to 124.20 $h^{-1}$, preferably 0.03 to 5.25 $h^{-1}$, most preferably 0.06 $h^{-1}$ (this corresponds to the volume of ammonia flowing through this reactor per hour and per volume of the reactor).

The "volume space velocity," for acetone in continuous operation is, in step (c), especially 0.15 to 1.33 $h^{-1}$, preferably 0.66 to 1.17 $h^{-1}$ (this corresponds to the volume of acetone flowing through this reactor per hour and per volume of the reactor).

The reaction in step (c) is preferably carried out at elevated temperature, especially at temperatures in the range of 20° C. to 180° C., preferably in the range of 40° C. to 100° C., particularly preferably in the range of 55° C. to 90° C., even more preferably in the range of 60° C. to 90° C. even more preferably at 75° C.

The reaction in step (c) is especially either carried out at the autogenous pressure of the components or at elevated pressure. Thus, the reaction in step (c) is preferably carried out at a pressure in the range of 1 to 16 bar, more preferably at a pressure in the range of 1 to 15 bar, even more preferably at a pressure in the range of 7 to 14 bar, even more preferably at 12 bar.

Ammonia is preferably metered in in step (c) of the inventive method as pure substance, i.e. as gas, and is especially present during the reaction dissolved in acetone or dissolved in the reaction mixture.

In step (c) of the inventive method, the acetone and/or mesityl oxide removed from RP1 in step (b) of the inventive method is used as reactant. In order to advantageously further shift the reaction to the side of the TAA, additional acetone can be added in step (c) of the inventive method.

Step (c) of the inventive method is carried out in the presence of a catalyst K2. All catalysts mentioned in the related art for this type of reaction are suitable as catalyst K2. In this case, the catalyst K2 can be homogeneous or heterogeneous, but is preferably heterogeneous.

All homogeneous catalysts described in the related art for this type of reaction are suitable as homogeneous catalyst K2, e.g. Brønsted acids, salts of these acids or Lewis acids, as described in EP 2 706 056 A1.

Preference is given, in cases in which K2 is a homogeneous catalyst, to said catalyst being selected from the group of ammonium salts, especially from the group comprising salts of ammonia and strong Brønsted acids [e.g. hydrochloric acid, sulfuric acid, nitric acid, organic acids (RCOOH) or sulfonic acids (RSO$_3$H), with R** being selected from the group consisting of saturated, unsaturated, branched, unbranched, ring-closed, open-chain aliphatic, aromatic, substituted or unsubstituted hydrocarbon radicals].

Preference is given, in cases in which K2 is a homogeneous catalyst, to said catalyst being ammonium nitrate. Ammonium nitrate has the advantage of being cheap, non-toxic, halide-free and hence less corrosive.

As catalyst K2, however, preference is given to using a heterogeneous catalyst, especially a solid acidic catalyst as for example described in DE 28 07 172 A1, CN 103224465 A or DE 10 2010 062 804 A1. These are catalysts which are practically insoluble in the reaction medium. For this purpose, preference is given to using a catalyst which is inorganic or organic and has active acid groups, preferably sulfonic ester groups or phosphoric ester groups.

K2 is accordingly especially selected from the group consisting of aluminium hydrosilicates of bentonite and/or montmorillonite type, inorganic ion exchangers based on aluminium silicate of zeolite type, mordenite type, erionite type or also diatomaceous earth treated with phosphoric acid at 700 to 1100° C., as described in CA 772 201.

Heterogeneous catalysts that are particularly preferred for K2 are ion exchange resins, especially cation exchange resins. These are preferably acidic.

Ion exchange resins for K2 include especially those which are inorganic-based (for example silicon dioxide) or organic-based (for example polystyrene or polystyrene copolymers, such as styrene-divinylbenzene copolymers), preferably organic-based, which have protic acid groups, especially alkylsulfonic ester groups, sulfonic ester groups (—SO$_3^-$), phosphoric ester groups, especially sulfonic ester groups.

A particularly preferred heterogeneous catalyst for K2 is selected from the following group:

A catalyst having a polymer resin, especially polystyrene or styrene-divinylbenzene copolymer, preferably polystyrene, and protic acids, especially —SO$_3^-$ groups, as functional groups (commercially available as Amberlyst® 15, Amberlite® 200, Lewatit® SP 120 or Lewatit® K2621); use may also be made alongside this of polystyrene sulfonate with the CAS number: 28210-41-5;

A catalyst having protic acids, especially sulfonic acid in polymeric form and which can be perfluorinated (described in DE 10 2010 062 804 A1. U.S. Pat. No. 4,831,146). This may for example be a sulfonated tetrafluoroethylene (CAS number: 31175-20-9) or a solid supported perfluorinated sulfonic acid in polymeric form with silicon dioxide as carrier material. Such catalysts are, inter alia, available under the trade names Nafion®, Aciplex® F, Femion®, Neosepta®, Fumion® F. A preferred catalyst is Nafion® SAC-13. Nafion® SAC-13 is porous silicon dioxide particles onto which Nafion® has been adsorbed in a charge of approximately 13 wt %;

Poly(2-acrylamido-2-methyl-1-propanesulfonic acid), sold as PolyAMPS® by Lubrizol.

Use is most preferably made, as K2, of a heterogeneous catalyst having a polymer resin, especially polystyrene or styrene-divinylbenzene copolymer, especially polystyrene, and protic acids, especially —SO$_3^-$ groups, as functional groups (commercially available as Amberlyst® 15, Amberlite® 200, Lewatit® SP 120 or Lewatit® K2621).

The amount of catalyst K2 used in step (c) is not particularly restricted and can be determined by those skilled in the art. Typically, if the catalyst is a homogeneous catalyst from the group of the Brønsted acids, salts of these acids or Lewis acids, preferably an ammonium salt, even more preferably is ammonium nitrate, the latter can be used in a molar ratio of ammonia to catalyst, preferably ammonium nitrate, in the range of 1:0.8 to 1:0.02. Most particularly preferably, the molar ratio of acetone:ammonia:ammonium nitrate is in the range of 7 to 8:0.9 to 1.1:0.085 to 0.098.

In the preferred embodiment, in which a solid, acidic ion exchanger is used for K2, the latter can be used as a fixed bed, for example in an amount of 10 to 20 vol % based on the total amount of the acetone and mesityl oxide used in step (c).

In step (c) of the inventive method, a crude product RP2 is then obtained which contains the desired product triacetone amine and optionally also the originally used reactant acetone and/or mesityl oxide, and also especially at least one by-product selected from the group consisting of diacetone alcohol, diacetone amine, acetonin, phorone, isophorone, preferably selected from the group consisting of diacetone alcohol, diacetone amine, acetonin and isophorone.

It goes without saying that RP2 can then in turn be subjected to a reaction step corresponding to reaction step (b) of the inventive method.

In a preferred embodiment of the inventive method, the catalyst K1 in step (a) and the catalyst K2 in step (c) of the inventive method are, independently of one another, a heterogeneous, even more preferably solid, acidic catalyst, more preferably as they were defined above. Most preferably of all, K1 and K2 are the same.

5. Removal of TAA

The removal of TAA from RP1 and/or RP2 may otherwise be carried out by crystallization, distillation, preferably with distillation, which takes place more preferably still in a downstream distillation column.

The following examples are intended to illustrate the invention without restricting it.

EXAMPLES

1. Reaction

Two cylindrical reactors connected in series were filled with Lewatit K2621 (polystyrene catalyst with —$SO_3^-$ as functional group, from Lanxess) such that this catalyst material was arranged delimited by screens above and below. The bed volume of the catalyst was in each case 600 ml in the moist with water state. The reactor was continuously charged with 630 g/h of acetone and 25 g/h of ammonia. A temperature of 75° C. and a pressure of 14 bar were set. The supply was in total 961.83 g (16.58 mol) of acetone. The LHSV (liquid hourly space velocity, i.e. the volume of reactants added per hour, relative to the reactor volume) was 0.03 to 0.06 $h^{-1}$ for the ammonia and 0.66 to 1.33 $h^{-1}$ for the acetone.

2. I1: Work-Up According to Inventive Method. i.e. with Hydrolysis 1 kg of the reactor output from the test according to point 1 were mixed with 3 to 5 wt % of water based on the amount of acetone used under point 1, and subsequently distillatively worked up on a rectification column. Distillation was carried out here for sufficient time that all light-boilers (acetone, mesityl oxide, diacetone alcohol, diacetone amine) were removed; TMDH pyridine and TAA and further highboilers formed were however removed from the bottom as waste products or products of value. Intermediate boilers such as acetonin and phorone were hydrolysed to as great an extent as possible into light-boiling components and were removable as a result.

Thereafter, the proportion of the different components in the bottom and in the distillate were determined by GC [column: HP-50 (30 m), temperature programme: 5° C./min 60-130° C., 15° C./min-270° C., 10 min]. The relative proportions of the respective components in the reactor output, distillate and bottom were determined and this is listed in the following table 1. In the following table 1, the components in the reaction output (with the exception of the water) are listed from left to right according to their boiling points ("NI"=not identified).

The first three rows give the area percentages (including water) of each component in the GC diagram.

The final row gives:

based on the total weight of the bottom product (200 g), the weights of the respective component in the bottom product were determined from the percentage proportion of the respective compound in the GC. The molar amount of the respective component in the bottom product and hence also the molar amount of acetone equivalents corresponding to the respective component can be calculated therefrom.

In this case, acetone corresponds to one acetone equivalent.

In this case, the following compounds correspond to two acetone equivalents: mesityl oxide (and isomer), diacetone alcohol, diacetone amine.

In this case, the following compounds correspond to three acetone equivalents: acetonin, phorone, isophorone.

TABLE 1

| Fractions | Acetone | Mesityl-oxide (and | Diacetone alcohol | Diacetone amine | TMDH pyridine | Acetonin | Phorone | NI | Triacetone amine | Isophorone | NI | Total | Water |
|---|---|---|---|---|---|---|---|---|---|---|---|---|---|
| Reactor output 1 kg (GC %) | 57.2 | 8.8 | 0.6 | 2.7 | 4.1 | 3.0 | 0.0 | 1.4 | 12.8 | 0.5 | 2.0 | 93.0 | 7.0 |
| Distillate 747 g | 61.5 | 19.4 | 0.1 | 0.6 | 2.3 | 0.1 | 0.0 | 1.3 | 0.0 | 0.0 | 0.0 | 85.4 | 14.6 |
| Bottom product 200 g | 0.2 | 1.8 | 0.7 | 2.2 | 10.9 | 4.4 | 0.5 | 1.0 | 66.5 | 0.3 | 11.4 | 99.8 | 0.2 |
| Acetone equivalent molar amount n(acetone) in mol (in bottom product) | 0.01 | 0.08 | 0.02 | 0.08 | | 0.18 | 0.03 | | | 0.009 | | 0.409 | |

The proportion of acetone equivalents lost in the inventive procedure based on the proportion of acetone used (16.58 mol) was thus determined and was 2.5%.

3. C1: Comparative Test without Hydrolysis

Test I1 was repeated without any water being added.

The corresponding contents of the respective components in the reactor output, distillate and bottom product and also the molar amount of acetone equivalents in the bottom product were determined as described for I1 and are listed in the following table 2 (NI=not identified).

TABLE 2

| Fractions | Acetone | Mesityl-oxide (and isomer) | Diacetone alcohol | Diacetone amine | TMDH pyridine | Acetonin | Phorone | NI | Triacetone amine | Isophorone | NI | Total | Water |
|---|---|---|---|---|---|---|---|---|---|---|---|---|---|
| Reactor output 1 kg | 57.2 | 8.8 | 0.6 | 2.7 | 4.1 | 3.0 | 0.0 | 1.4 | 12.8 | 0.5 | 2.0 | 93.0 | 8.4 |
| Distillate 750 g | 68.8 | 10.1 | 0.5 | 0.9 | 3.8 | 1.5 | 0.0 | 0.8 | 0.6 | 0.0 | 0.0 | 85.7 | 10.0 |
| Bottom product 192 g | 0.0 | 0.0 | 0.0 | 4.8 | 3.3 | 9.8 | 0.0 | 4.5 | 58.0 | 3.1 | 12.7 | 96.1 | 1.8 |
| Acetone equivalent molar amount n in mol in bottom product | 0.0 | 0.0 | 0.0 | 0.16 | | 0.37 | 0.0 | | | 0.114 | | 0.644 | |

It was thereafter determined that 3.9% of the acetone equivalents used were in the bottom product and thus were lost for further reaction steps with ammonia.

4. Results 4.1) In I1 (distillate: 747 g; bottom product 200 g) and in C1 (distillate: 750 g; bottom product: 192 g) virtually the same proportion of distillate and bottom product were able to be recovered;

4.2) The content of TAA in the bottom product was higher in I1 than in C1, i.e. the absolute yield of TAA was better in the case of the inventive procedure.

4.3) The proportion of acetone equivalents not lost to the bottom product and hence able to react is higher in the inventive procedure according to I1. The fact that in I1 (table 1) a proportion of acetone, mesityl oxide and diacetone alcohol was still found in the bottom product with a simultaneously reduced proportion of acetonin and isophorone moreover points to the fact that in the inventive procedure these higher molecular weight by-products had obviously been cleaved to give acetone or mesityl oxide, whereas this is not the case with the conventional procedure (C2; table 2). It is critical that the total content of acetone equivalents in the bottom product in C1 is higher than the total content of acetone equivalents in the bottom product in I1.

The invention claimed is:

1. A method for preparing triacetone amine, comprising:
(a) reacting acetone and ammonia in the presence of a first catalyst (K1) at a temperature of 20 to 180° C. and a pressure of 1 to 16 bar to give a first crude product (RP1) comprising triacetone amine, acetone, mesityl oxide and at least one by-product selected from the group consisting of diacetone alcohol, diacetone amine, acetonin, phorone and isophorone,
(b) at least partially removing, by distillation, the acetone and/or the mesityl oxide from RP1,
(c) adding ammonia and, optionally, further acetone, to the acetone and/or the mesityl oxide removed from RP1 in (b), and at least partially reacting the added ammonia with the acetone and/or the mesityl oxide in the presence of a second catalyst (K2) at a temperature of 20 to 180° C. and a pressure of 1 to 16 bar to give triacetone amine, as a result of which a second crude product (RP2) comprising triacetone amine is obtained,
(d) adding water to RP1 before and/or during the removing, by distillation, of the acetone and/or the mesityl oxide from RP1 in (b), and
(e) removing triacetone amine,
wherein at least one of the by-products in RP1 is at least partially reacted with the water, and
wherein at least one of the by-products in RP1 is at least partially cleaved into mesityl oxide and/or acetone, and
wherein said first and said second catalyst are each independently selected from the group consisting of a Brønstead acid, a salt of a Brønstead acid, a Lewis acid and a solid acidic catalyst.

2. The method according to claim 1, wherein, in (d),
the water is added to RP1 during the removing, by distillation, of the acetone and/or the mesityl oxide from RP1 in (b),
wherein at least one of the by-products in RP1 is at least partially reacted with the water, and
wherein at least one of the by-products in RP1 is at least partially cleaved into mesityl oxide and/or acetone.

3. The method according to claim 1, wherein the at least partially removing, by distillation, of the acetone and/or the mesityl oxide from RP1 in (b) takes place in a distillation column.

4. The method according to claim 3, wherein a temperature range used in the distillation in (b) is below the boiling point of triacetone amine.

5. The method according to claim 1, wherein a molar ratio of the acetone used in (a) to the ammonia used in (a) is 3:1 to 20:1.

6. The method according to claim 1, wherein K1 is a solid acid catalyst.

7. The method according to claim 1, wherein the amount of water added in (d) is ≥0.1 wt %, based on the sum of the weights of phorone, diacetone alcohol, diacetone amine, acetonin and isophorone contained in RP1.

8. The method according to claim 1, wherein K2 is a solid acid catalyst.

9. The method according to claim 1, wherein, in (c), the ammonia is added in an overall amount such that, for each mole of the acetone used in (c), 0.05 to 0.33 mol of ammonia is added, and in addition to the ammonia added for the acetone, for each mole of the mesityl oxide used in (c), 0.1 to 0.66 mol of the ammonia is added.

10. The method according to claim 1, wherein, in (d), reaction is at a temperature <205° C.).

11. The method according to claim 1, wherein, in (d), reaction is at a temperature range of 30 to 200° C.).

12. The method according to claim 1, wherein, in (d), reaction is at a temperature range of 70 to 185° C.

* * * * *